United States Patent [19]
Gilmour

[11] Patent Number: 6,142,964
[45] Date of Patent: Nov. 7, 2000

[54] MULTI-PLANAR BRACE

[75] Inventor: Robert Farrer Gilmour, Auckland, New Zealand

[73] Assignee: Bodyworks Properties Limited, Auckland, New Zealand

[21] Appl. No.: 09/049,192

[22] Filed: Mar. 27, 1998

[30] Foreign Application Priority Data

Mar. 27, 1997 [NZ] New Zealand .......................... 314500

[51] Int. Cl.[7] ..................................................... A61F 5/00
[52] U.S. Cl. ................................. 602/20; 602/16; 602/21
[58] Field of Search .................................. 602/5, 16, 20, 602/21, 23, 24, 26, 27; 128/878, 881, 882

[56] References Cited

U.S. PATENT DOCUMENTS 4,881,532  11/1989  Borig et al. .
5,086,760   2/1992  Neumann et al. .
5,782,783   7/1998  Young et al. ............................. 602/20
5,848,979  12/1998  Bonutti et al. ........................ 602/21 X

FOREIGN PATENT DOCUMENTS 2 184 659    7/1987  United Kingdom .
WO 91/13604  9/1991  WIPO .
WO 95/23568  9/1995  WIPO .
WO 96/40017 12/1996  WIPO .

*Primary Examiner*—Stephen R. Crow
*Assistant Examiner*—Denise Pothier
*Attorney, Agent, or Firm*—Young & Thompson

[57] ABSTRACT

A brace includes a first engagement element adapted to engage or be engaged with part of the body to one side of a body joint and a second engagement element adapted to engage or be engaged with part of the body to the other side of the body joint. A joint is provided between the first engaging element and the second engaging element which joint is capable of movement in more than one plane, usually three planes. The joint is able to be clamped in the selected position.

4 Claims, 1 Drawing Sheet

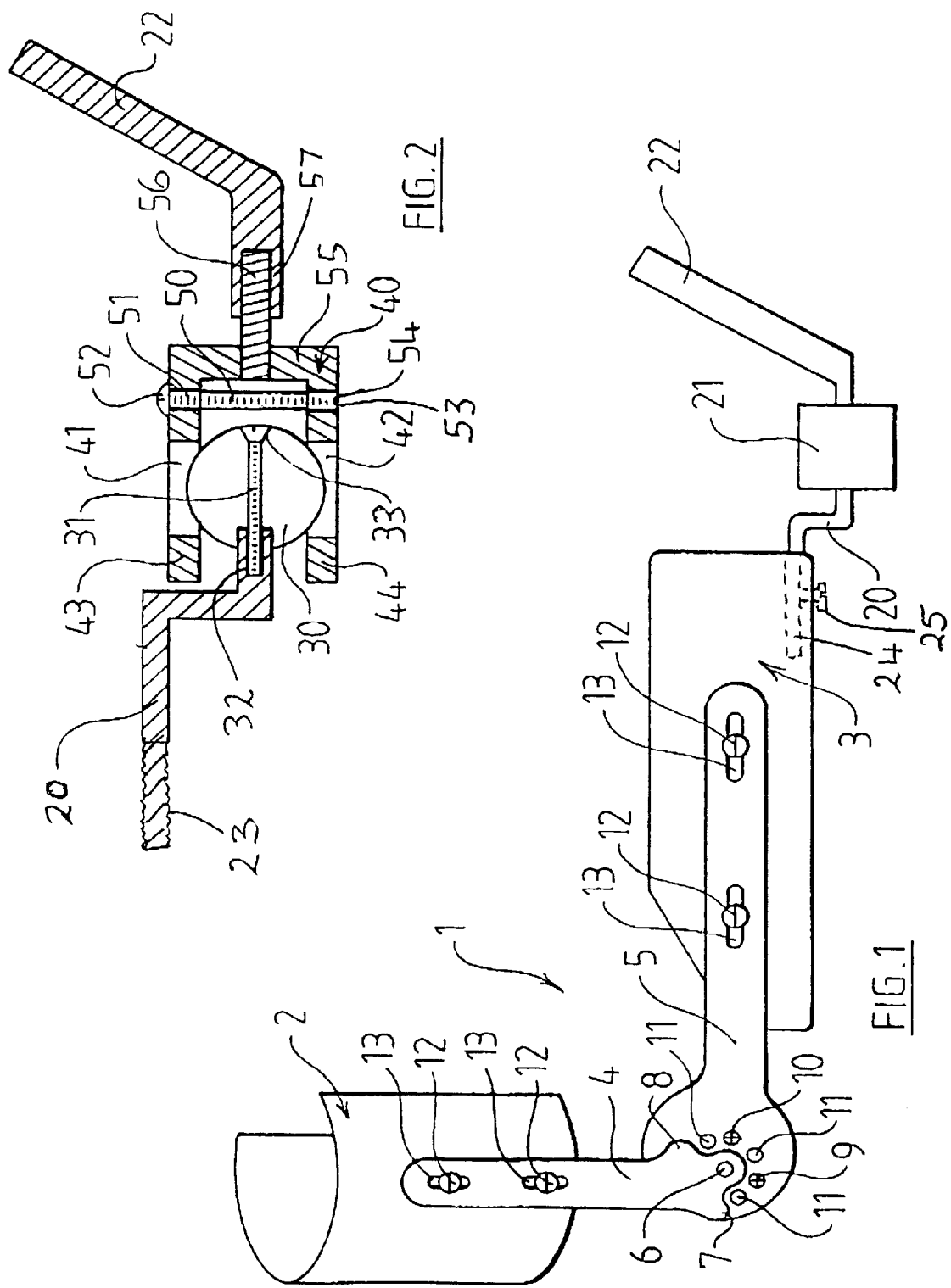

MULTI-PLANAR BRACE

BACKGROUND OF THE INVENTION

1. Field of the Invention

This invention relates to a brace and has been devised as a brace to allow optimal positioning of a multi-planar body joint.

2. Description of the Related Art

A multi-planar joint such as for example a wrist, but also an elbow, ankle, hip, or shoulder, allows relative movement of body parts in more than one plane. Using the wrist as an example the wrist is capable of radial and ulna deviation, flexion and extension, and pronation and supination. Thus for example the wrist flexes and extends that is to say folds down and cocks back up, or deviates from side to side, or the whole forearm can rotate relative to the upper arm thus for example the forearm supinates (palm up) and pronates (palm down). Again by reference to the wrist, the intention of a brace is to immobilise the upper arm and allow early supervised exercise of joints in order to prevent stiffness and also prevent prolonged rehabilitation periods. At present braces of this type only allowed the wrist to be placed in an anatomically neutral position.

It would be advantageous however to immobilise the limb with the wrist in a position which is optimal for a specific fracture or soft tissue procedure. Also a neutral wrist position may be detrimental and this would prevent the use of existing devices. Similar considerations apply to the other multi-planar joints as mentioned above.

SUMMARY OF THE INVENTION

It is therefore an object of the present invention to provide a brace which will go at least some distance towards meeting the foregoing requirements in a simple yet effective manner or which will at least provide the public with an option.

Accordingly in one aspect the invention consists in a brace comprising first engagement means adapted to engage or be engaged with part of the body to one side of a body joint, a second engagement means adapted to engage or be engaged with part of the body to the other side of the body joint, a joint between the first engaging means and the second engaging means, the joint being capable of movement in more than one plane.

Preferably the joint is capable of movement in at least three planes.

Preferably the joint comprises a ball and socket joint.

Preferably the body joint comprises the wrist, ankle, hip, or shoulder.

Preferably the body joint is the wrist.

Preferably a clamp is provided to maintain the joint in a selected position.

Preferably the dimensions of the brace are such that the joint is at the level of the body joint axis.

Preferably the joint is off-set from the longitudinal axis of the body part.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

One preferred form of the invention will now be described with reference to the accompanying drawings in which, FIG. 1 is a diagrammatic side elevation of a brace according to one preferred form of the invention with the tie down parts of the brace not shown for the purposes of clarity, FIG. 2 is a diagrammatic view of the joint part of the brace according to one preferred form of the invention.

DESCRIPTION OF THE PREFERRED EMBODIMENT

Referring to the drawings a brace 1 is provided which comprises a first engagement means 2 adapted to engage the upper arm above the elbow and a second engagement means 3 adapted to engage or be engageable with part of the forearm below the elbow. The invention herein described will be described with reference to the wrist. Of course some reconstruction particularly to the parts of the device which engage the body will be necessary in respect of the alternative body joints, This can be achieved by the use of known techniques.

For the purpose of clarity the parts of the brace which enable the first and second engagement means to be held to the body parts are not shown in the drawing, but for example the parts 2 and 3 may have suitable wrap around and cushioning structures as are known in the art, to engage the parts 2 and 3 to the upper and lower arms respectively. Extending between the parts 2 and 3 are a pair of members 4 and 5 connected together by pivot 6. The construction is desirable such that the range of movement of the members 4 and 5 is limited for example by providing stops 7 and 8 and pins 9 and 10 between which physical contact may be made. The pins 9 and 10 may be moved between a number of apertures 11. Such a construction is a known type of arm brace to control movement of the elbow. The position of the engagement means 2 and 3 on the members 4 and 5 may be varied for example by screws or other devices such as 12 engageable into the parts 2 and 3 which are able to be moved in slots such as 13 and be tightenable onto the material of the members 4 and 5 again substantially in the known manner.

Extending outwardly from the part 3 is an arm 20 which is engaged with a joint 21. The joint 21 carries a handle or other grip 22 which, where the body joint is a wrist, is able to be gripped by the hand or palm of the user. The part 20 is able to be moved relative to the member 3, for example by providing the member 20 with a screw thread 23 which engages into a threaded socket, indicated at 24, in the member 3. Alternatively the member 20 may slide into a recess. In each case the movement is restricted by use of a clamp such as a screw 25.

The end of the member 20 remote from the engagement means 3 carries part of the joint and in the embodiment described this comprises a ball 30 which may be fixed to the member 20 for example by screw 31 passing into a threaded aperture 32 in the end of the member 20 being secured by a counter-sunk aperture 33 in the ball. A bifurcated member 40 is provided which has apertures or depressions 41 and 42 in the arms 43 and 44 of the bifurcated member 40. The ball 30 sits in the apertures 41 and 42. This enables the bifurcated member 40 to move relative to the member 20. This movement is multi-planar and a clamp is provided so that the joint can be clamped into the desired position. In one simple form the clamp may take the form of a bolt 50 passing through an aperture 51 in the member 40 of size such that head 52 of the bolt 50 will not pass through the aperture 51 but so that the distal end 53 of the bolt 50 is positioned in a threaded aperture 54 in member 40. Thus by tightening the bolt 50 the arms 43 and 44 are drawn together thereby clamping the periphery of the apertures 41 and 42 onto the ball 30. The clearances between the ball 30 and the edges of the apertures 41 and 42 are exaggerated in FIG. 2 for clarity. Extending outwardly from the mid point of the back 55 of the member 40 is a threaded rod 56 onto which the hand grip 22 is positioned. The threaded rod 56 engages into a threaded aperture 57.

The construction is such that both the distance from the palm to the elbow and the palm to the wrist is able to be adjusted to meet the size of the individual user. In respect of hand grip 22 this may be achieved by moving the rod 20 in the recess 24. The member 20 may have a square or rectangular cross-section at the free end thereof which fits into a correspondingly shaped depression in the ball 30 so as to minimise the risk of any relative rotation of these two parts.

The joint is offset substantially as shown in the drawings in order to allow free movement and the distance between the palm post 22 and the joint must be anatomically accurate so that the universal joint is at the level of the wrist axis. If the joint is not offset it could dig into the ulna side of the wrist.

The clamp will also need to extend a minimal distance beyond the contact point with the ball or rotary motion will be limited.

In use the engagement means 2 and 3 are engaged with the arms of a user about the elbow. The palm of the user engages the handle 22 and the wrist is moved into the desired position by rotation of the ball 30 relative to the bifurcated member 40. When the desired position has been achieved, the clamp, for example the bolt 50, is tightened until the joint is immobilised therefore substantially immobilising the wrist.

Should it be desired to alter the relative position of the wrist the clamp may be loosened, the wrist reset and the joint reclamped.

Thus it can be seen that a brace is provided which has the advantage that a multi-planar joint can be set to a position other than an anatomically neutral position. As previously described this has advantages in allowing a wrist position which is optimal for a specific fracture or soft tissue procedure. Similar braces will allow similar advantages for ankle, elbow, shoulder and hip multi-planar joints.

What we claim is:

1. A brace for attachment to a user's body, comprising first engagement means adapted to engage or be engaged with an upper arm above an elbow of the user, a second engagement means having a length adapted to engage or be engaged with a forearm below the elbow of the user, a first joint between the first engagement means and the second engagement means, the first joint allowing an angle between the first engagement means and the second engagement means to be varied and held in a selected position, a grip extending in the lengthwise direction away from an outer edge of the second engagement means able to be held by a hand of the user, a second joint between the second engagement means and the grip, the second joint comprising a ball and socket joint capable of movement in more than one plane, and a clamp adapted to maintain the second joint in a selected position.

2. A brace as claimed in claim 1 wherein the second joint is capable of movement in at least three planes.

3. A brace as claimed in claim 1 wherein the second joint lies outside an extension of an outer edge of the second engagement means.

4. A brace as claimed in claim 1, wherein a distance between the first joint and the second joint can be varied and held at a selected length.

* * * * *